United States Patent [19]

Winner

[11] Patent Number: Plant 6,065

[45] Date of Patent: Dec. 22, 1987

[54] VARIETY OF GERANIUM NAMED VALERIE

[75] Inventor: Blair L. Winner, Lompoc, Calif.

[73] Assignee: Denholm Seeds, Lompoc, Calif.

[21] Appl. No.: 800,808

[22] Filed: Nov. 22, 1985

[51] Int. Cl.[4] ..... A01H 5/00
[52] U.S. Cl. ..... Plt./68
[58] Field of Search ..... Plt./68

*Primary Examiner*—Robert E. Bagwill

*Attorney, Agent, or Firm*—Webb, Burden, Robinson & Webb

[57] ABSTRACT

A new geranium cultivar is distinguished by its excellent conformation with compact growth and excellent basal branching. The foliage is moderate in size, with numerous attractive, well placed leaves. The flowers are long lasting, persistent and large and well placed relative to the foliage. The flower color is a brilliant, luminescent salmon-orange.

1 Drawing Figure

BACKGROUND OF THE NEW PLANT

The present invention comprises a new and distinct cultivar of *Pelargonium hortorum* which is a zonal geranium known by the varietal name Valerie. The new variety (Oglevee No. 885, Denholm No. 42091-1) was discovered in a selective breeding program by Mr. Blair L. Winner and is a selection from the crossing of a dwarf early flowering scarlet selection (Denholm No. 34235-9) by the unpatented cultivar "Sincerity."

The new cultivar was discovered in August of 1982 at Denholm Seeds in Lompoc, Calif., was first asexually reproduced by cuttings by Denholm Seeds at Lompoc, Calif., and has been repeatedly asexually reproduced by cuttings at Oglevee Associates, Inc. in Connellsville, Pa. over a 36 month period. It has also been trial and field tested at Connellsville, Pa. during the summers of 1983, 1984 and 1985. It has been found to retain its distinctive characteristics through successive propagations.

The new cultivar is more compact, more floriferous and has improved basal branching as compared with the cultivar "Sincerity." The salmon-orange coloring also differs from the scarlet red of the cultivar "Sincerity" and the number selection.

The new cultivar, when grown in a glass greenhouse in Connellsville, Pa. using full natural light, 60° F. night temperature, 68° F. day temperature and 71° F. vent temperature and grown in a soilless media of constant fertilizer of 275–300 parts per million nitrogen and potassium, has a response time from a rooted cutting to a flowering plant in a 10 cm pot of six weeks.

DESCRIPTION OF THE DRAWING

The accompanying drawing illustrates the new cultivar, the color being as true as possible with color illustrations of this type.

DESCRIPTION OF THE NEW PLANT

The following detailed descriptions set forth the characteristics of the cultivar. The data which define these characteristics were collected from asexual reproductions carried out by Oglevee Associates, Inc. in Connellsville, Pa. The plant histories were taken on plants blossomed under natural light in a greenhouse and color readings were taken indoors under 200 foot candles of cool, white fluorescent light. Color references are primarily to the R.H.S. Colour Chart of The Royal Horticultural Society of London.

THE PLANT

Classification:
- *Botanical.*—*Pelargonium hortorum.*
- *Commercial.*—Zonal geranium.

Form: Bush; compact; semi-dwarf; free basal branching; blooms close to foliage.
Height: 21–25 cm from media surface.
Growth: Free branching from base; short internodes.
Strength: Stands upright without artificial support.
Foliage: Stalked leaf attachment. Faint zone.
Leaves:
- *Size.*—6.5–8.0 cm across.
- *Shape.*—Reniform; cordate base.
- *Margin.*—Crenate.
- *Texture.*—Pubescent; dull.
- *Color.*—Top: outer — green group 137C; center — green group 139C. Bottom: green group 143C.
- *Ribs and veins.*—Palmate venation; yellow-green group 145B.

Petioles: Green group 143C.
Stem:
- *Color.*—Yellow-green group 144A.
- *Internodes.*—1.5–3.0 cm in length.

THE BUD

Shape: Upright; hemispherical cluster.
Size: 3–4 cm across.

INFLORESCENCE

Blooming habit: Continuous; upright; semi-double; little shatter; hemispherical in shape.
Size: 9.5–11.5 cm across.
Borne: Umbel; florets on pedicel; pedicels on peduncle; 3–6 cm above foliage.
Florets:
- *Form.*—Round; cupped to slightly flat, with petaloids; regular.
- *Color.*—Top; Red group 40B; eye: Red-purple group 67C. Bottom: Red group 38D.
- *Petals.*—Palmate venation; 5–8 in number; separate — not united; 2–3 petals with purplish eye; obovate; margin entire.
- *Size.*—3.5–4.5 cm across.
- *Texture and appearance.*—Smooth surface; sparkling reflective flecks, flat.

Petaloids:

*Quantity.*—2–4.

*Shape.*—Long linear — some lobed.

*Color.*—Front: Red group 40B. Back: Red group 38D.

Pedicel:

*Length.*—1.5–2.0 cm in length.

*Color.*—Yellow-green group 145B.

Peduncle: Arises from node; opposite leaf petiole; 11–15 cm in length; yellow-green group 144A.

Disease resistance: Moderate resistance to Botrytis.

REPRODUCTIVE ORGANS

Stamens, anthers: Yellow when immature.

Filaments; Flat; white at base to reddish purple at tip; irregular length.

Pollen: Golden yellow initially; dark brown later.

Pistils:

*Number.*—1 with 5 part stigma.

*Length.*—6–8 mm.

Stigma: 5 part; red-purple; 2 mm.

Style: Single; red-purple; 2 mm in length.

Ovaries: 3–5 mm in length; yellow-green; very pubescent (0.1–0.5 mm); superior.

Fruit: None observed.

The new cultivar is of excellent conformation with compact growth and excellent basal branching. The foliage is moderate in size, with numerous attractive, well placed leaves and numerous long lasting, persistent, large flowers, well placed relative to the foliage. The brilliant, luminescent salmon-orange flower color is unique.

The new cultivar has been fingerprinted by Dr. Richard Craig and his associates at Penn State University in State College, Pa. The fingerprinting was conducted on a Waters High Performance Liquid Chromatograph equipped with an automatic injection system, dual pumps, solvent programmer, data module, variable wavelength detector, and a $C_{18}$ column. The anthocyanin and flavonol chemical markers utilizing flower petals as an adjunct for cultivar identification were determined.

The anthocyanin and flavonol concentrations of petals just after anthesis of cultivar Valerie florets sampled in April of 1985 are compared with cultivar "Glacier Crimson" (U.S. Plant Pat. No. 5,057) and presented below in Tables 1 and 2. Results are based on the average of multiple tests. It should be noted that changes in environment can influence the biosynthesis.

TABLE 1

| | Anthocyanin Concentration ug anthocyanin 3,5 diglucoside/g fresh wt. | | | | | |
|---|---|---|---|---|---|---|
| Cultivar | Delphinidin | Cyanidin | Pelargonidin | Peonidin | Malvidin | Total |
| VALERIE | —[z] | 40 | 1524 | 524 | t[y] | 2093 |
| XCR - Bruni | — | 78 | 5251 | 2418 | — | 7747 |

—[z] = not detected.
t[y] = trace < 10 ug.

TABLE 2

| | Flavonol Concentration ug/g fresh wt. | | | | | |
|---|---|---|---|---|---|---|
| Cultivar | Qu3-[z] rhagal | Qu3-rut | Qu3-gal | Qu3-glu | Km3-rhagal | Km3-gal |
| VALERIE | t | 20 | —[w] | t | 188 | 23 |
| XCR - Bruni | 11 | 34 | — | t | 307 | 47 |

| Cultivar | Km3-rut | Km3-xyl | Km3-arab | Km3-rha | Total |
|---|---|---|---|---|---|
| VALERIE | 706 | t | 30 | 93 | 1075 |
| XCR - Bruni | 1257 | 13 | 49 | 185 | 1908 |

[z]Abbreviations: Km = Kaempferol; Qu = Quercetin; arab = arabinoside; gal = galactoside; glu = glucoside; rha = rhamnoside; rhagal = rhamnosylgalactoside; rut = rutinoside; xyl = xyloside.
—[w] = not detected.
t = trace < 10 ug.

I claim:

1. A new and distinct variety of geranium plant substantially as herein shown and described and parts therefor.

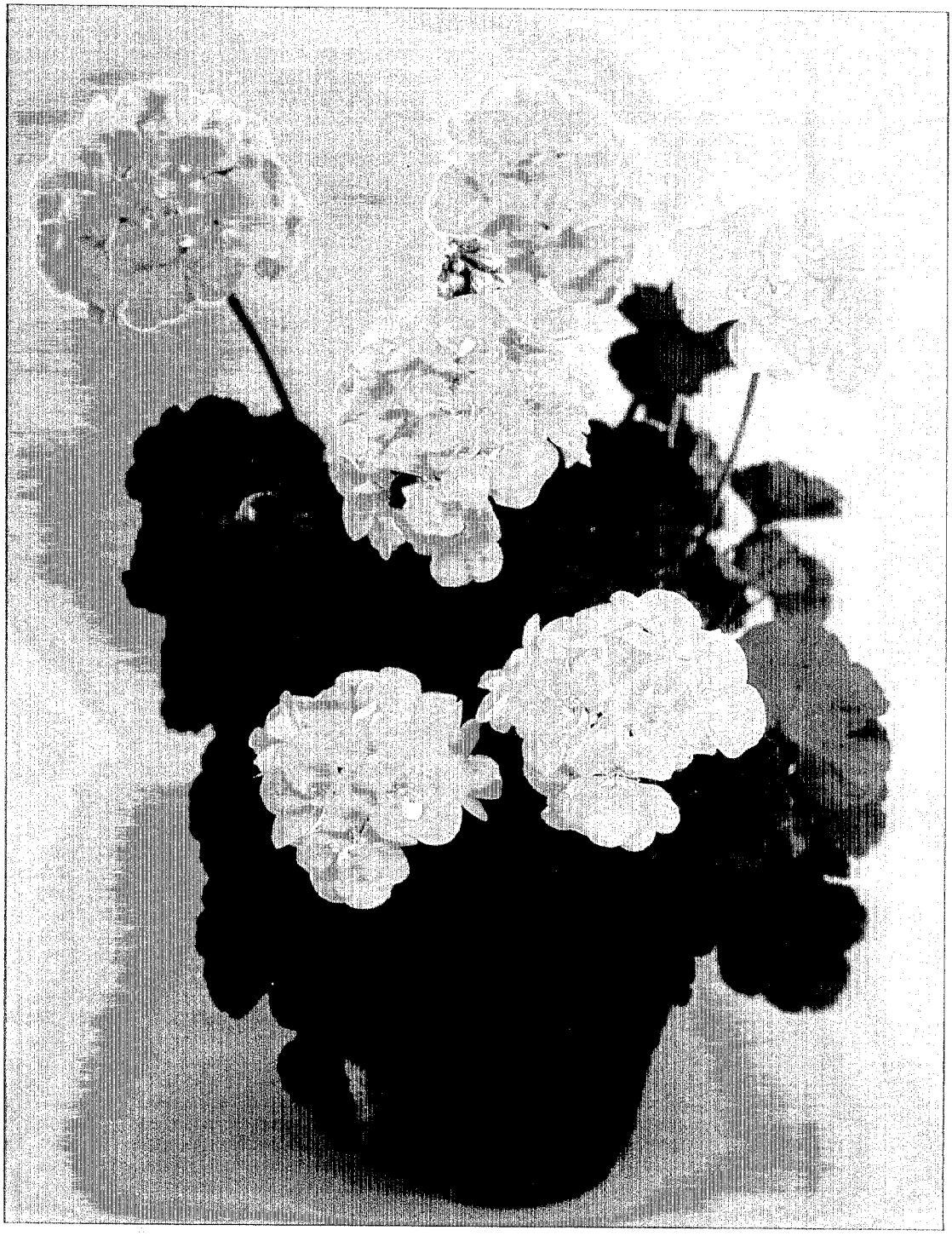

* * * * *